(12) United States Patent
Hsu et al.

(10) Patent No.: US 6,246,906 B1
(45) Date of Patent: *Jun. 12, 2001

(54) SYSTEM AND METHOD FOR TREATING ATRIAL ARRHYTHMIAS

(75) Inventors: William Hsu, Circle Pines; Bruce H. KenKnight, Maple Grove, both of MN (US)

(73) Assignee: Cardiac Pacemakers, Inc., St. Paul, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/044,651

(22) Filed: Mar. 19, 1998

(51) Int. Cl.[7] .............................. A61N 1/362; A61N 1/39
(52) U.S. Cl. .................................. 607/4; 607/13; 607/14
(58) Field of Search ..................... 607/4, 13–15

(56) References Cited

U.S. PATENT DOCUMENTS

| | | | |
|---|---|---|---|
| 3,937,226 | * | 2/1976 | Funke . |
| 4,548,203 | | 10/1985 | Tacker Jr. et al. .................... 128/419 |
| 4,559,946 | | 12/1985 | Mower .............................. 128/419 D |
| 4,662,382 | | 5/1987 | Sluetz et al. ......................... 128/785 |
| 4,708,145 | | 11/1987 | Tacker, Jr. et al. .............. 128/419 D |
| 4,775,950 | | 10/1988 | Terada et al. ......................... 364/578 |

(List continued on next page.)

FOREIGN PATENT DOCUMENTS

| | | |
|---|---|---|
| 0436517 | 7/1991 | (EP) . |
| 0467652 | 1/1992 | (EP) .............................. A61N/1/368 |
| 0522693 | 1/1993 | (EP) . |
| 0588124 | 3/1994 | (EP) . |
| 0594269 | 4/1994 | (EP) . |
| 0606688 | 7/1994 | (EP) . |
| 0770412 | 5/1997 | (EP) . |
| 0813886 | 12/1997 | (EP) . |
| 95/28987 | 11/1995 | (WO) .............................. A61N/1/39 |
| 95/28988 | 11/1995 | (WO) .............................. A61N/1/39 |
| 97/01373 | 1/1997 | (WO) .............................. A61N/1/39 |

OTHER PUBLICATIONS

Allessie, M., et al., "Regional Control of Atrial Fibrillation by Rapid Pacing in Conscious Dogs", *Circulation*, 84 ( 4 ), pp. 1689–1697, (Oct. 1991).

Ayers, G.M. et al., "Ventricular Proarrhythmic Effects of Ventricular Cycle Length and Shock Strength in a Sheep Model of Transvenous Atrial Defibrillation", *Circulation*, 89( 1), pp. 413–422, (Jan. 1994).

Kenknight, B.H., et al., "Regional Capture of Fibrillating Ventricular Myocardium", *Circulation Research*, 77( 4), pp. 849–855, (Oct. 1995).

*Primary Examiner*—William E. Kamm
*Assistant Examiner*—Carl H. Layno
(74) *Attorney, Agent, or Firm*—Schwegman, Lundberg, Woessner & Kluth, P.A.

(57) ABSTRACT

A system for defibrillating an atrial region of a heart experiencing a supraventricular arrhythmia. The defibrillation system senses and analyzes both atrial and ventricular cardiac signals of the heart to determine if the heart is experiencing a supraventricular arrhythmia. Upon detecting a supraventricular arrhythmia, the defibrillation system begins delivering a train of atrial pacing pulses to the atria of the heart and a series of ventricular pacing pulses to the ventricles of the heart to synchronize the contractions of the heart with the pacing pulses. The defibrillation system then delivers a defibrillation electrical energy pulse across the atrial region at a predetermined coupling interval time after delivering a final atrial pacing pulse and a final ventricular pacing pulse so that the defibrillation pulse will fall outside the occurrence of a T-wave of the heart, thus reducing the likelihood of inducing ventricular fibrillation.

31 Claims, 5 Drawing Sheets

U.S. PATENT DOCUMENTS

| | | | |
|---|---|---|---|
| 4,787,389 | 11/1988 | Tarjan | 128/419 |
| 4,788,980 | 12/1988 | Mann et al. | 128/419 PG |
| 4,800,883 | 1/1989 | Winstrom | 128/419 D |
| 4,827,932 | 5/1989 | Ideker et al. | 128/419 D |
| 4,984,572 | 1/1991 | Cohen | 128/419 D |
| 4,996,984 | 3/1991 | Sweeney | 128/419 D |
| 5,085,213 | 2/1992 | Cohen | 128/419 D |
| 5,154,485 | 10/1992 | Fleishmann | 297/445 |
| 5,161,528 | 11/1992 | Sweeney | 128/419 D |
| 5,178,140 | 1/1993 | Ibrahim | 128/419 D |
| 5,193,536 * | 3/1993 | Mehra . | |
| 5,265,600 | 11/1993 | Adams et al. | 607/4 |
| 5,282,836 | 2/1994 | Kreyenhagen et al. | 607/4 |
| 5,282,838 | 2/1994 | Hauser et al. | 607/9 |
| 5,350,401 | 9/1994 | Levine | 607/4 |
| 5,366,485 | 11/1994 | Kroll et al. | 607/5 |
| 5,370,667 | 12/1994 | Alt | 607/19 |
| 5,403,355 | 4/1995 | Alt | 607/9 |
| 5,431,682 | 7/1995 | Hedberg | 607/5 |
| 5,431,685 | 7/1995 | Alt | 607/6 |
| 5,441,521 | 8/1995 | Hedberg | 607/6 |
| 5,458,622 | 10/1995 | Alt | 607/15 |
| 5,464,429 | 11/1995 | Hedberg et al. | 607/4 |
| 5,466,245 | 11/1995 | Spinelli et al. | 607/17 |
| 5,489,293 | 2/1996 | Pless et al. | 607/5 |
| 5,522,853 | 6/1996 | Kroll | 607/5 |
| 5,549,642 | 8/1996 | Min et al. | 607/5 |
| 5,609,613 | 3/1997 | Woodson et al. | 607/19 |
| 5,620,468 | 4/1997 | Mongeon et al. | 607/5 |
| 5,690,686 | 11/1997 | Min et al. | 607/5 |
| 5,713,924 * | 2/1998 | Min et al. | 607/4 |
| 5,797,967 | 8/1998 | KenKnight et al. | 607/4 |
| 5,840,079 * | 11/1998 | Warman et al. | 607/4 |

* cited by examiner

SYSTEM AND METHOD FOR TREATING ATRIAL ARRHYTHMIAS

TECHNICAL FIELD

The present invention relates generally to implantable medical devices and in particular to the use of implantable medical devices for treating supraventricular tachyarrhythmias.

BACKGROUND OF INVENTION

Clinically, atrial arrhythmias are one of the most frequently encountered of the cardiac arrhythmias. Annually, more than 500,000 individuals are diagnosed with atrial arrhythmias, including atrial fibrillation, flutter and tachycardia. While these conditions are not immediately life-threatening, they can lead to serious health risks if left untreated. These include the increased potential for developing chronic fibrillation, embolic strokes and for transferring the aberrant atrial electrical signals to the ventricles, which can result in ventricular tachycardia and/or ventricular fibrillation.

Treating atrial fibrillation has traditionally involved the use of antiarrhythmic agents. However, patients who have experienced only one episode or infrequent paroxysmal episodes of atrial fibrillation may not want the inconvenience of daily medication and follow-up. Alternatively, patients with recurrent episodes are at the highest risk for a thromboembolism and often are candidates for maintenance antiarrhythmic and anticoagulation therapies. This long-term therapy, however, can have potential drawbacks as chronic use of some antiarrhythmic agents may have toxic side effects. As a result, effective alternatives to chronic pharmacological treatment have been sought.

Implantable atrial cardioverter/defibrillators are a potential solution to acutely treat atrial fibrillation. The implantable atrial cardioverter/defibrillators sense and analyze atrial cardiac signals to detect the occurrence of an atrial arrhythmia. Once an atrial arrhythmia is detected, the device can deliver a low energy discharge of cardioverting/defibrillating electrical energy across the atria of the heart in an attempt to terminate the arrhythmia and to restore normal sinus rhythm. In designing these devices, investigators have also proposed synchronizing the delivery of the atrial defibrillation pulse to the sinus rhythm of the ventricles so as to avoid triggering a ventricular arrhythmia. While these suggested methods attempt to prevent inducing a ventricular arrhythmia, there remains the possibility of inducing a ventricular tachyarrhythmia or a ventricular fibrillation by inadvertently delivering a cardioverting/defibrillating electrical energy pulse during a T-wave that resulted from an aberrant ventricular contraction. Therefore, a need still exists for a system to safely and reliably treat a supraventricular arrhythmia.

SUMMARY OF THE INVENTION

The present invention provides an improved defibrillation system and method for safely and reliably treating supraventricular arrhythmias. The defibrillation system and method respond to a detected supraventricular arrhythmia by delivering a train of atrial pacing pulses and a series of ventricular pacing pulses in a synchronized manner. The invention is unique in that the defibrillation system synchronizes and coordinates the ventricles and the atria of the heart using the synchronized pacing pulses prior to defibrillating the atria such that the defibrillation electrical energy pulse is delivered so as to avoid occurring during a ventricular T-wave, thus reducing the likelihood of inducing a ventricular tachyarrhythmia or ventricular fibrillation.

According to one embodiment of the present invention there is provided a system including an implantable housing; a ventricular catheter; an atrial catheter; and electronic control circuitry within the implantable housing and coupled to the ventricular and atrial catheters for identifying and analyzing cardiac signals and for providing electrical energy to the heart to affect sinus rhythm of the heart in response to a signal from the electronic control circuitry indicating the occurrence of an atrial arrhythmia.

The ventricle catheter of the defibrillator system has at least one ventricular pacing electrode on its peripheral surface, which is electrically connected to the electronic control circuitry within the implantable housing. In one embodiment, the ventricular catheter has a first ventricular electrode and a second ventricular electrode for sensing and pacing the ventricle of the heart. In an additional embodiment, the ventricle catheter is positioned within the heart with the ventricle pacing electrodes in an apex location of a right ventricle chamber of the heart.

The atrial catheter has at least one atrial pacing electrode and at least one defibrillation electrode, both of which are electrically connected to the electronic control circuitry. In one embodiment, the atrial catheter has an atrial pacing electrode and a defibrillation electrode for sensing, pacing and defibrillating the atria of the heart. In an additional embodiment, the atrial catheter is positioned in the heart with the atrial pacing electrode in a supraventricular region of the heart and the defibrillation electrode in the right atrium chamber or a major vein leading to the right atrium of the heart.

According to one embodiment of the method of defibrillating the atria of the heart, when a supraventricular arrhythmia is detected, the electronic control circuitry delivers a synchronized pacing scheme of atrial and ventricular pacing pulses. The synchronized pacing scheme begins with an initial concurrent atrial and ventricular pacing pulse. The defibrillation system then proceeds to deliver a synchronized train of atrial pacing pulses through the atrial pacing electrode. In an alternative embodiment, the synchronized pacing scheme begins with a first atrial pacing pulse from the train of atrial pacing pulses being delivered to an atrial region of the heart upon detecting a ventricular R-wave through the ventricular catheter. Concurrent with delivering the train of atrial pacing pulses to the atrial region of the heart, the defibrillation system and method also deliver a series of ventricular pacing pulses to the ventricular region of the heart through the ventricular catheter.

The series of ventricular pacing pulses delivered to the ventricular region of the heart are synchronized with the delivery of the train of atrial pacing pulses to the atrial. The synchronization of the pacing pulses to the atrial and ventricular regions of the heart is based on a 1 to "n" ratio of ventricular pacing pulses to atrial pacing pulses, where "n" is an integer value greater than or equal to 3 and less than or equal to 50. The series of ventricular pacing pulses delivered to the ventricles help to stabilize the ventricular rhythm prior to the delivery of the atrial defibrillation electrical energy pulse.

At a predetermined coupling interval time after delivering a final atrial pacing pulse and a final ventricular pacing pulse, the atrial defibrillation electrical energy pulse is delivered across the atria of the heart. This atrial defibrillation pulse is timed so that the defibrillation electrical energy pulse falls outside the occurrence of a ventricular T-wave, thus reducing the chance of inducing ventricular fibrillation. As a result, the synchronized atrial defibrillation pulse of the present invention provides for a safer manner of treating atrial arrhythmias.

DETAILED DESCRIPTION

In the following detailed description, reference is made to the accompanying drawings which form a part hereof and in which is shown by way of illustration specific embodiments in which the invention may be practiced. These embodiments are described in sufficient detail to enable those skilled in the art to practice and use the invention, and it is to be understood that other embodiments may be utilized and that electrical, logical, and structural changes may be made without departing from the spirit and scope of the present invention. The following detailed description is, therefore, not to be taken in a limiting sense and the scope of the present invention is defined by the appended claims and their equivalents.

Figure 1:
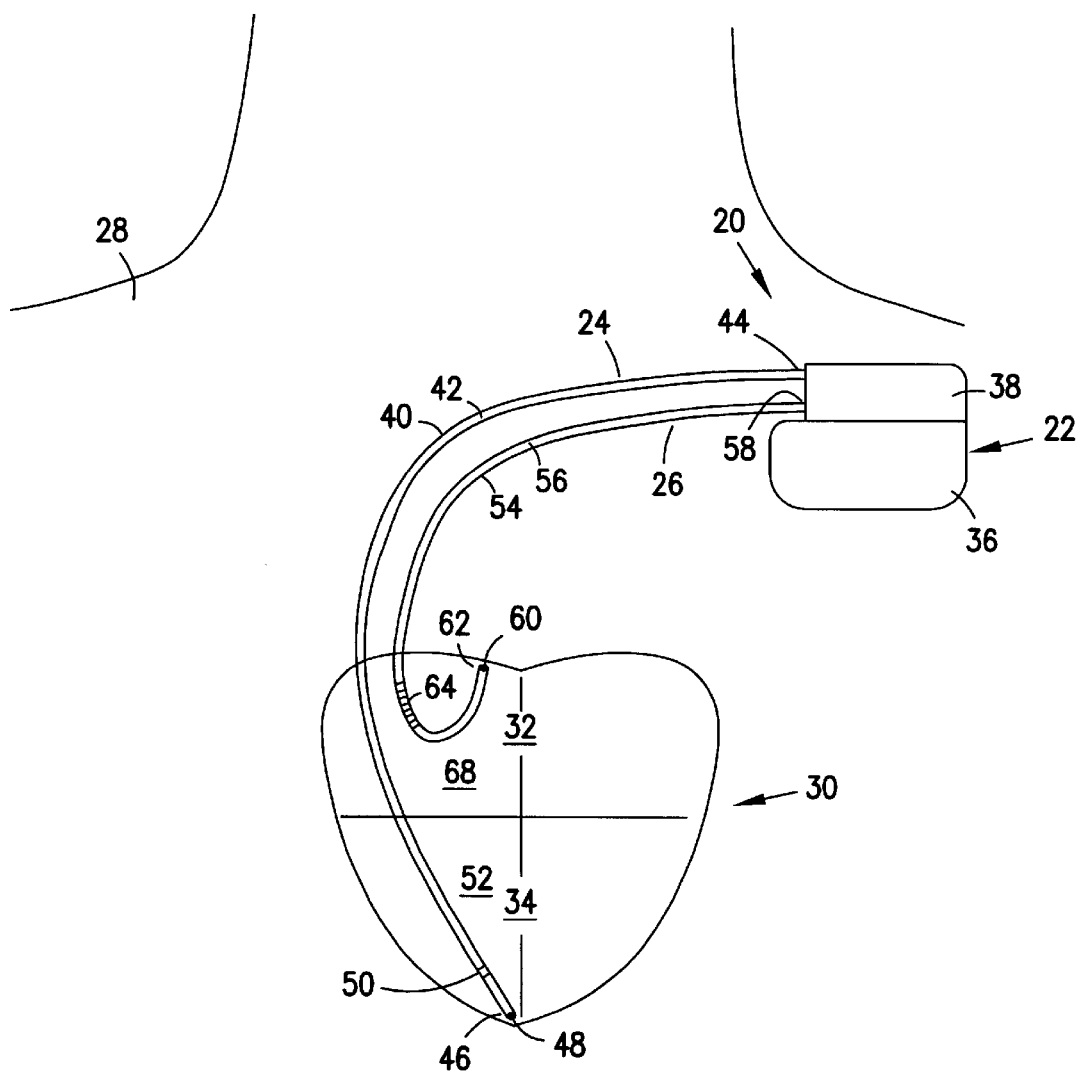
FIG. 1 is a schematic diagram of one embodiment of a defibrillation system of the present invention with an atrial lead and a ventricular lead implanted in a human heart from which segments have been removed to show details.

Referring now to FIG. 1 of the drawings, there is shown one embodiment of a defibrillation system 20 including an implantable pulse generator 22 physically and electrically coupled to a ventricular catheter 24 and an atrial catheter 26, which defibrillation system 20 may be used in practicing the method according to the present invention. The defibrillation system 20 is implanted in a human body 28 with portions of the atrial catheter 26 and the ventricular catheter 24 inserted into a heart 30 to detect and analyze electric cardiac signals produced by both the atria 32 and the ventricles 34 of the heart 30 and to provide electrical energy to the heart 30 under certain predetermined conditions to treat atrial arrhythmias of the heart 30.

Figure 2:
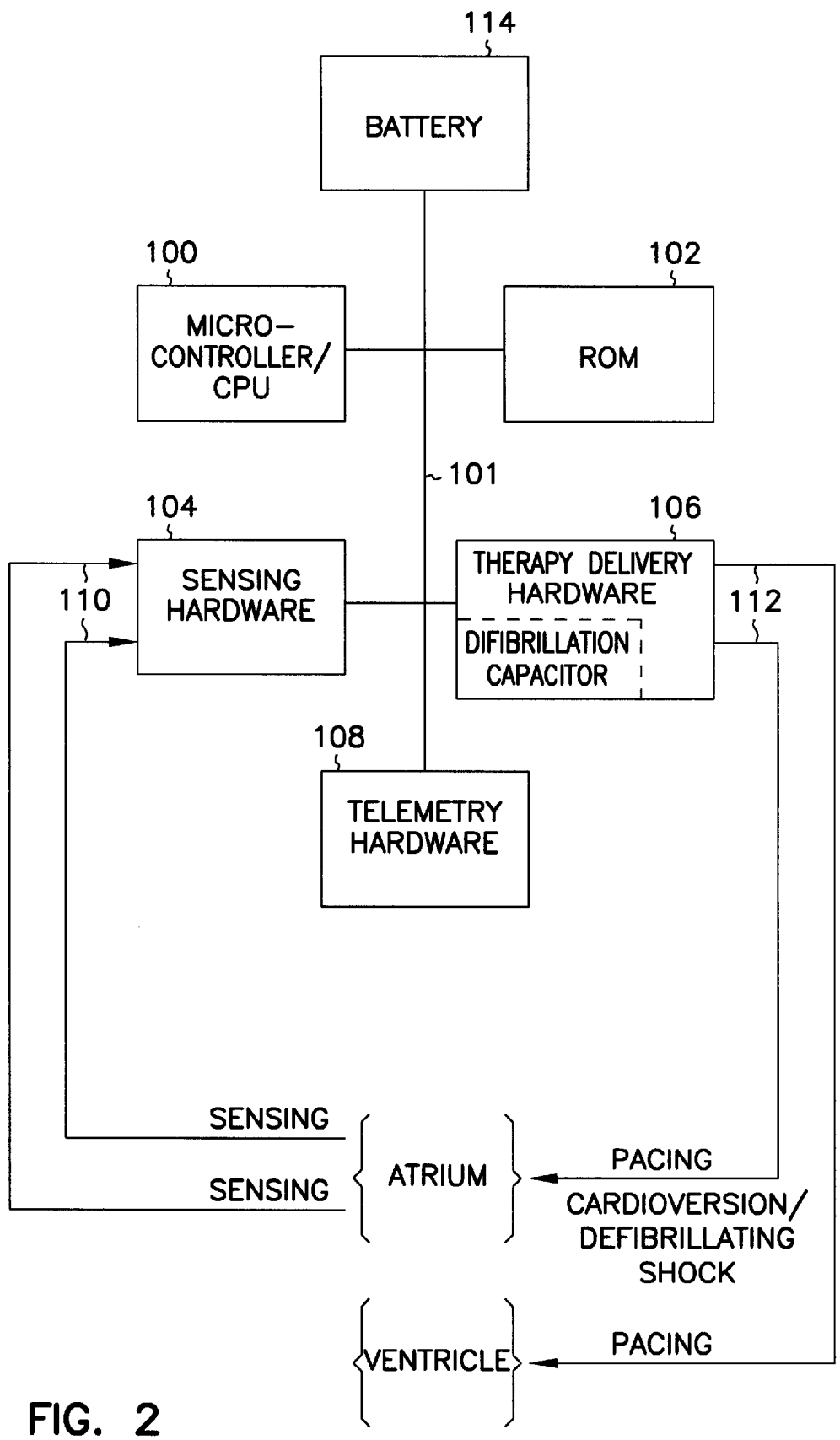
FIG. 2 is a schematic of one embodiment of electronic control circuitry according to the present invention.

A schematic of the implantable pulse generator 22 electronics is shown in FIG. 2. The implantable pulse generator 22 comprises an implantable housing 36 which contains electronic control circuitry, including a microprocessor 100, read only memory (ROM) 102, sensing hardware 104, including sense amplifiers, therapy delivery hardware 106, including a defibrillation capacitor, and telemetry hardware 108. All electronic components of the implantable pulse generator 22 are interconnected by way of a bus connection 101. Within the ROM 102 the algorithm of the present invention is implemented as firmware and is executed by the microprocessor 100. The sensing hardware 104 is also connected to the microprocessor 100, and contains a plurality of electrical connections 110 coupled to the sense amplifiers. The output of the sense amplifiers is connected to the microprocessor 100, so that the atrial 32 and the ventricular 34 cardiac signals received through the sensing hardware 104 are analyzed by the algorithm within the microprocessor 100.

The microprocessor 100 is also coupled to the therapy delivery hardware 106, which controls the delivery of electrical energy to the heart 30 through a plurality of electrical output connections 112 to affect the sinus rhythm of the heart 30 under certain combinations of atrial 32 and ventricular 34 conditions. Power to the implantable pulse generator 22 is supplied by an electrochemical battery 114 that is housed within the implantable pulse generator 22. The implantable pulse generator 22 is interrogated and programmed via bi-directional radio frequency telemetry through the telemetry hardware 108 with an external programmer.

Referring again to FIG. 1, a connector block 38 is mounted on the implantable pulse generator 22. In one embodiment, the connector block 38 has two connector ports to physically and electrically connect the atrial catheter 26 and the ventricular catheter 24 to the sensing hardware 104 and the therapy delivery hardware 106 of the implantable pulse generator 22. Additional connector ports can be added to the connector block 38, and configurations with three or more ports can be employed. Alternatively, the connector block can be provided with one connector port for physically and electrically connecting an implantable transvenous catheter to the implantable pulse generator 22.

The electrical activity in the heart 30 is sensed and therapies are delivered to the heart 30 through at least one transvenous pacing and defibrillation lead connected to the implantable pulse generator 22. Unipolar and/or bipolar pacing and sensing electrodes are used in conjunction with the at least one transvenous pacing and defibrillation lead. In the embodiment shown in FIG. 1, a bipolar lead is utilized for sensing ventricular activity and a unipolar lead is utilized for sensing atrial activity. Sensing the atrial activity includes determining the occurrence of atrial P-waves, and sensing the ventricular activity includes determining the occurrence of ventricular R-waves.

The defibrillation system 20 also has at least one defibrillation electrode on the atrial catheter 26 which is connected to the plurality of electrical output connections 112, and serves to deliver defibrillation level, or cardioversion level, electrical pulses to the atria of the heart 30 upon a signal from the microprocessor 100 indicating a predetermined condition within the heart 30. The level of defibrillation electrical energy pulse delivered to the atrial region of the heart 30 is a programmable value set between 1 to 10 Joules. Other defibrillation electrical energy levels are possible, however, and can include values that are less than 1 Joules or greater than 10 Joules.

In one embodiment, the implantable housing 36 of the defibrillation system 20 is a defibrillation electrode and defibrillation electrical pulses are delivered to the atria between the defibrillation electrode on the atrial catheter 26 and the implantable housing 36 of the implantable pulse generator 22. In one embodiment, the implantable housing 36 of the implantable pulse generator 22 has an exposed electrically conductive surface that is electrically connected to an anode of the therapy delivery hardware 106. All defibrillation electrical pulses are delivered to the heart with at least two defibrillation electrodes, or through at least one defibrillation electrode and the implantable housing 36 of the implantable pulse generator 22 where the defibrillating electrical energy provided to the patient's heart is a biphasic pulse delivered between the exposed electrically conductive surface of the implantable housing and the defibrillation electrode. Additionally, the biphasic pulses delivered between exposed electrically conductive surface of the implantable housing and the defibrillation electrode are asymmetric with a first phase of the biphasic pulse having a greater amplitude than the second phase of the biphasic pulse. The defibrillation system 20 also supports a plurality of sensing and pacing regimens for both the atria and the ventricles, including DDDR pacing, which are known in the art.

Referring now to FIG. 1, there is shown an embodiment of the ventricular catheter 24 having an elongate body 40, a peripheral surface 42, proximal and distal ends, 44 and 46, and at least one ventricular pacing electrode connected to the electronic control circuitry. In one embodiment, the ventricular catheter 24 has a first ventricular electrode 48 and a second ventricular electrode 50 on the peripheral surface 42. The first ventricular electrode 48 and the second ventricular electrode 50 receive bipolar electrical cardiac signals from a right ventricular chamber 52 of the heart 30, and are attached on the peripheral surface 42 of the elongate body 40.

The first ventricular electrode 48 is at or adjacent to the distal end 46 of the elongate body 40 and is either a pacing tip electrode or a semi-annular electrode partially encircling or an annular electrode encircling the peripheral surface 42 of the elongate body 40. The second ventricular electrode 50 is an annular electrode encircling or a semi-annular electrode partially encircling the peripheral surface 42 of the elongate body 40. The second ventricular electrode 50 is spaced longitudinally along the peripheral surface 42 from the first ventricular electrode 48 and the distal end 46 of the ventricular catheter 24 is positioned within the right ventricular chamber 52 of the heart 30 with the first ventricular electrode 48, in one embodiment, located in an apex location of the right ventricular chamber 52 of the heart 30.

Electrical leads extend longitudinally within the elongate body 40 of the ventricular catheter 24 from a connection end at the proximal end 44 and make connection to the first and second ventricular electrodes 48 and 50. The proximal end 44 of the ventricular catheter 24 is releasably attached to the connector block 38 of the implantable pulse generator 22 with the contact ends of the electrical leads in electrical connection with both the sense amplifiers of the sensing hardware 104 and the therapy delivery hardware 106 such that the implantable pulse generator receives bipolar signals from and delivers bipolar pacing to the right ventricular chamber 52 of the heart 30.

In a further embodiment, the atrial catheter 26 is shown comprising an elongate body 54 having a peripheral surface 56, a proximal end 58, a distal end 60, and at least one atrial pacing electrode and at least one defibrillation electrode, both of which are located on the peripheral surface 56 of the elongate body 54. Referring to FIG. 1, there is shown one embodiment of the atrial catheter 26 having an atrial pacing electrode 62 and a defibrillation electrode 64. In one embodiment, the defibrillation electrode 64 is a defibrillation coil electrode as are known in the art. The atrial pacing electrode 62 is at or adjacent the distal end of the elongate body 54 where it receives unipolar electrical cardiac signals from a right atrial chamber 68 of the heart 30.

Both the atrial pacing electrode 62 and the defibrillation electrode 64 are attached on the peripheral surface of the elongate body 54 where the defibrillation electrode 64 is spaced apart and spaced longitudinally from the atrial pacing electrode 62 on the peripheral surface 56 of the atrial catheter 26. In one embodiment, the atrial catheter 26 is positioned within the heart 30 with the atrial pacing electrode 62 and the defibrillation electrode 64 in the supraventricular region of the heart 30, where the distal end 60 of the atrial catheter 26 is located within the right atrial chamber 68 of the heart 30 to afford positioning the atrial pacing electrode 62 on an endocardial wall of the right atrial chamber 68 and the defibrillation electrode 64 positioned within the right atrial chamber 68 or a major vein leading to the right atrium of the patient's heart. Suitable location for the atrial pacing electrode 62 includes the right atrial appendage, high right atrium or ostium of the coronary sinus. Alternatively, the distal end 60 of the atrial catheter 26 is located within a coronary vein of the patient's heart, including a coronary sinus or a great vein, to position the atrial pacing electrode 62 adjacent to the left atrium chamber of the heart 30, and the defibrillation electrode 64 within the right atrial chamber 68 or a major vein leading to right atrium.

In an alternate embodiment, the atrial catheter has a second atrial pacing electrode attached to the peripheral surface of the elongate body where the first atrial pacing electrode 62 is at or adjacent to the distal end 60 of the elongate body 54 and is either a pacing tip electrode or a semi-annular electrode partially encircling or an annular electrode encircling the peripheral surface 56 of the elongate body 54. The second atrial pacing electrode is an annular electrode encircling or semi-annular electrode partially encircling the peripheral surface 56 of the elongate body 54 and allows the defibrillation system 20 to provide bipolar sensing and pacing to the supraventricular region of the heart 30.

In an additional embodiment, the atrial catheter 26 includes two defibrillation electrodes on the peripheral surface 56 of the elongate body 54 where the two defibrillation electrodes are spaced apart and spaced longitudinally along the peripheral surface 56 of the atrial catheter 26 to afford positioning the atrial catheter 26 within the coronary sinus of the patient's heart 30 with the atrial pacing electrode 62 and the two defibrillation electrodes within the supraventricular region of the patient's heart. In one embodiment, the atrial pacing electrode 62 is adjacent to the left atrial chamber of the heart 30, one of the two defibrillation electrodes within the coronary sinus of the heart 30, and the second defibrillation electrode within the right atrial chamber 68 or a major vein leading to right atrial chamber 68 of the heart 30.

Besides the lead configuration shown in FIG. 1, the defibrillation system 20 supports several other lead configurations and types. For example it is possible to use ventricular epicardial rate sensing, atrial endocardial bipolar pace/sensing, ventricular endocardial bipolar pace/sensing, epicardial patches, single body transvenous leads with two or more defibrillation electrodes and at least one pacing electrode, and ancillary leads in conjunction with the implantable pulse generator 22.

In one embodiment, the defibrillating electrical energy provided to the patient's heart are biphasic pulses delivered between the defibrillation electrode 64 and the implantable housing 36 of the implantable pulse generator 22. In an alternative embodiment, the defibrillating electrical energy provided to the heart are biphasic pulses delivered between the two defibrillation electrodes. In a further embodiment, the two defibrillation electrodes are electrically connected such that the defibrillating electrical energy provided to the heart are biphasic pulses delivered between the electrically connected defibrillation electrodes and the exposed electrically conductive surface of the implantable housing 36.

Referring once again to FIG. 1, electrical leads extend longitudinally within the elongate body 54 of the atrial catheter 26 from a connection end at the proximal end 58 to make connection with the atrial pacing electrode 62 and the defibrillation electrode 64. The proximal end 58 of the atrial catheter 26 is releasably attached to the connector block 38 of the implantable pulse generator 22 with the contact ends of the electrical leads in electrical connection with the electronic control circuitry, including both the sense amplifiers of the sensing hardware 104 and the therapy delivery hardware 106 such that the implantable pulse generator 22 receives unipolar signals from the atria 32 of the heart 30 and delivers unipolar pacing and defibrillation electrical energy pulses to the atria 32 of the heart 30.

The ventricular catheter 24 and the atrial catheter 26 are releasably attached to and are separated from the implantable pulse generator 22 to facilitate inserting the ventricular catheter 24 and the atrial catheter 26 into the heart 30. The ventricular and atrial catheters, 24 and 26, are inserted into the heart 30 transvenously through a cephalic or subclavian vein to position the distal end 60 of the atrial catheter 26 in the supraventricular region of the heart 30 and the distal end 60 of the ventricular catheter 24 in the apex of the right ventricular chamber 52. The proximal end 58 of the atrial catheter 26 and the proximal end of the ventricular catheter 24 are then attached to the implantable pulse generator 22. The proximal end 58 of the atrial catheter 26 and the proximal end 58 of the ventricular catheter 24 are adapted to seal together with the connector ports of the implantable pulse generator 22 to thereby engage the contact ends of the atrial catheter 26 and the ventricular catheter 24 with the plurality of electrical connections 110 and the therapy delivery hardware 106 of the implantable pulse generator 22. The implantable pulse generator 22 of the defibrillation system 20 is then positioned subcutaneously within the human body 28.

Figure 3:
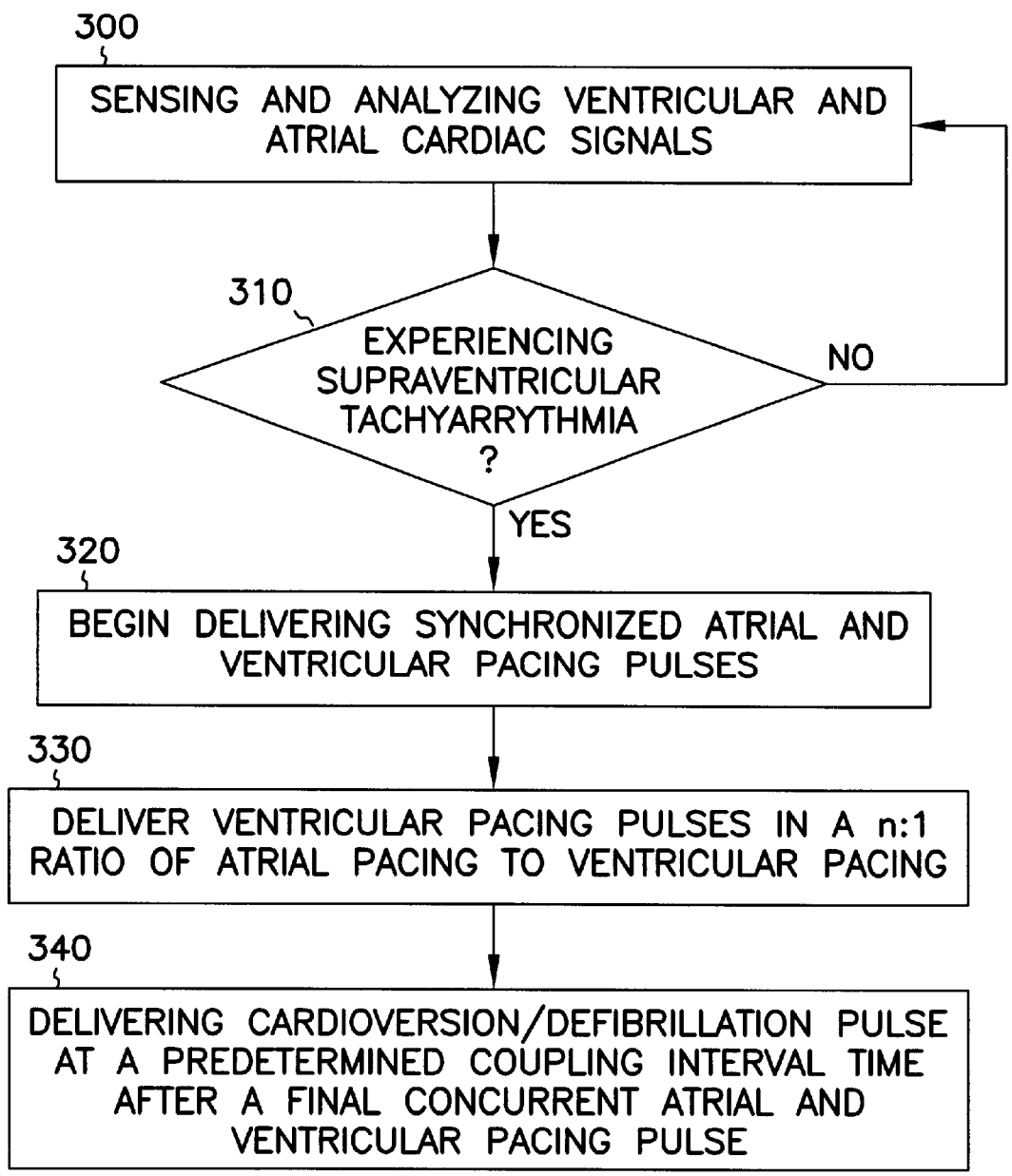
FIG. 3 is a flow diagram of one embodiment of the method according to the present invention.

Referring now to FIG. 3, there is shown a flow diagram of one embodiment of the method used by the defibrillation system 20 for treating a supraventricular arrhythmia of a patient's heart. Initially at 300, the defibrillation system 20 utilizes the ventricular catheter 24 and the atrial catheter 26 for sensing the ventricular and atrial cardiac signals of the heart 30. The electronic control circuitry receives either unipolar or bipolar cardiac signals through the ventricular and atrial pacing electrodes. The sensed cardiac signals are then analyzed by the defibrillation system 20 at 310 to determine if the heart is experiencing a supraventricular arrhythmia. In this context a supraventricular arrhythmia can include atrial tachyarrhythmias and atrial fibrillation.

In one embodiment, the electronic control circuitry of the defibrillation system 20 determines the occurrence and/or presence of supraventricular arrhythmias at 310 by analyzing the structure of the P-wave detected by the defibrillation system 20. In an alternative embodiment, the rate relation of the atrial P-waves and the ventricular R-waves is used to determine if the heart 30 is experiencing a supraventricular arrhythmia. In one embodiment, the presence of an atrial fibrillation is indicated when the defibrillation system 20 detects both an atrial rate that is greater than 200 beats per minute and the absence of a ventricular arrhythmia. In one embodiment, the absence of a ventricular arrhythmia is indicated when the ventricular rate is less than 150 beats per minute as detected by the ventricular catheter 24.

During 310, if the heart is not experiencing a supraventricular arrhythmia, the defibrillation system 20 returns to 300 to analyze the next series of sensed ventricular and atrial intervals. If, however, a supraventricular arrhythmia is detected at 310, the defibrillation system 20 proceeds to 320 where the electronic control circuitry of the defibrillation system 20 functions to deliver the synchronized atrial and ventricular pacing pulses over a programmable pacing scheme duration. In one embodiment, the programmable pacing scheme duration is the time during which the synchronized atrial and ventricular pacing pulses are delivered to the heart 30. During the programmable pacing scheme duration, the defibrillation system 20 charges the defibrillation capacitor to a predetermined energy level. At the conclusion of the programmable pacing scheme duration the therapy delivery hardware 106 is then prepared to deliver at least one atrial defibrillation level shock to the supraventricular region of the heart 30. The programmable pacing scheme duration is a programmable value that is set in the range between 2 to 30 seconds.

At the beginning of the programmable pacing scheme duration, the defibrillation system 20 starts the synchronized atrial and ventricular pacing pulses by delivering a train of atrial pacing pulses to an atrial region of the heart and a series of ventricular pacing pulses to a ventricular region of the heart, where the series of ventricular pacing pulses is synchronized with the train of atrial pacing pulses. In one embodiment, the delivery of the synchronized train of atrial pacing pulses and the series of ventricular pacing pulses begin with an initial concurrent atrial and ventricular pacing pulse. In an alternative embodiment, the delivery of the synchronized atrial and ventricular pacing pulses begins with the defibrillation system 20 initially delivering a first atrial pacing pulse of the train of atrial pacing pulses. A first ventricular pacing pulse synchronized with the train of atrial pacing pulses is then subsequently delivered to the heart. In one embodiment, the first atrial pacing pulse of the train of atrial pacing pulses is delivered during a ventricular R-wave detected by the defibrillation system 20.

The electronic control circuitry is programmed to deliver a set number of atrial pacing pulses during the train of atrial pacing pulses, where the number of atrial pacing pulses is programmed in the range of between approximately 10 to 1000 pacing pulses. Additional ranges for the number of atrial pacing pulses are also possible, for example the number of atrial pacing pulses can be selected from the ranges of between 20 to 70 or 30 to 50 pacing pulses. The atrial pacing pulses of the train of atrial pacing pulses are also delivered to the atrium at a programmable atrial pacing interval. The programmable atrial pacing interval is set to a value between approximately 20 to 50 milliseconds per pacing pulse. Other programmable atrial pacing interval ranges are possible, however, and by way of example can include values between 25 to 50, 25 to 45, 20 to 40, or 30 to 40 milliseconds per atrial pacing pulse.

In one embodiment, the defibrillation system 20 delivers the train of atrial pacing pulses across the atrial pacing electrode 62 to an atrial region of the heart 30. The energy level of the pacing pulses of the train of atrial pacing pulses are a programmable value set between 0.01 to 1 Joules. Other pacing pulse energy levels are possible, however, and can include values that are less than 0.01 or greater than 1 Joules.

Concurrent with the delivery of the train of atrial pacing pulses, the electronic control circuitry of the defibrillation system 20 at step 330 also delivers a series of ventricular pacing pulses across the ventricular pacing electrodes to a ventricular region of the heart 30. In one embodiment, the pacing rate of the series of the ventricular pacing pulses is a programmable value, where the ventricular pacing rate is programmed at a pacing rate that is at least 10 beats per minute above the patient's intrinsic ventricular rate. The concurrent delivery of the series of ventricular pacing pulses is synchronized with the train of atrial pacing pulses. In one embodiment, to synchronize the ventricular and atrial pacing pulses, each ventricular pacing pulse of the series of ventricular pacing pulses is synchronized to occur with every nth atrial pacing pulse of the train of atrial pacing pulses, where n is a programmable integer value greater than or equal to 3 and less than or equal to 50. The number of atrial pacing pulses in the train of atrial pacing pulses must also be divisible by n such that the result is an integer value (e.g., atrial train equal to 50, n equal to 5 and ventricular series equal to 10 pacing pulses). This synchronized pacing scheme allow the defibrillation system 20 to issue a concurrent atrial and ventricular pacing pulse every n atrial pacing pulse, and allows for a final atrial pacing pulse of the train of atrial pacing pulses and a final ventricular pacing pulse to be delivered to the heart.

In one embodiment, the final atrial pacing pulses and the final ventricular pacing pulse are delivered substantially simultaneously to the heart. This synchronization of the atrial and ventricular pacing pulse trains organizes and synchronizes the contraction of both the atria and the ventricles of the heart 30 in such a way that ventricular pacing pulses and a subsequent atrial defibrillation electrical energy pulse is delivered to the heart outside of a ventricular T-wave, thus reducing the likelihood of inducing ventricular fibrillation.

In one embodiment of the present invention, the term substantially simultaneously constitutes pacing pulses that are delivered within at least 5 ms of each other. However, in an alternative embodiment, a delay in delivering the final atrial and final ventricular pacing pulse is programmed into the defibrillation system, such that the final ventricular pacing pulse is delivered prior to delivering the final atrial pacing pulse. This programmed delay in delivering the final atrial and final ventricular pulse is programmed by the physician or clinician into the defibrillation system base up each individual patient's cardiological condition.

In an additional embodiment, the defibrillation system 20 monitors the ventricular region of the heart prior to delivering the final concurrent atrial and ventricular pacing pulse to determine if a premature ventricular contraction has occurred. In this context, a premature ventricular contraction is any ventricular contraction, indicated by a sensed R-wave, that occurs subsequent to the most recently paced ventricular contraction. In other words, the defibrillation system 20 monitors the heart 30 to ensure that a previously detected ventricular R-wave was the result of a ventricular pacing pulse delivered by the defibrillator system 20, and not the result of a premature ventricular contraction. This consideration may be important as it has been suggested that if the R-wave interval just prior to delivering an atrial defibrillation shock was too short in duration, possibly due to a premature ventricular contraction, the chances of inducing a ventricular arrhythmia from the shock may be higher.

If the most recently detected R-wave just prior to delivering the atrial defibrillation shock was a premature ventricular contraction, the defibrillation system 20 in one embodiment repeats the entire pacing scheme of delivering the train of atrial pacing pulses to the atrial region of the heart 30 and the series of ventricular pacing pulses to a ventricular region of the heart 30 again. In an alternative embodiment, the defibrillation system 20 delivers a predetermined number of additional atrial pacing pulses and ventricular pacing pulses to the heart 30 upon detecting a premature ventricular contraction. The defibrillation system 20 delivers the additional atrial and ventricular pacing pulses according to the same synchronized pacing scheme used in delivering the train of atrial pacing pulses and the series of ventricular pacing pulses. Upon completing delivery of the additional atrial and ventricular pacing pulses, the defibrillation system 20 monitors the ventricular region of the heart 30 prior to delivering the final atrial pacing pulse and the final ventricular pacing pulse to determine if a premature ventricular contraction has occurred. The predetermined number of additional atrial pacing pulses is a programmable number set in the range between 10 to 1000 pacing pulses, and the number of additional ventricular pacing pulses are determined by and are synchronized to occur with every nth pacing pulse of the additional atrial pacing pulses, where n is a programmable integer value greater than or equal to 3 and less than or equal to 50.

After the synchronized atrial and ventricular pacing pulses have been delivered to the heart 30, the defibrillation system 20 terminates the supraventricular arrhythmia at step 340 by delivering a defibrillation pulse of electrical energy at a predetermined coupling interval time after the final concurrent atrial pacing pulse and ventricular pacing pulse across the atria 32 region of the heart 30.

In one embodiment, the defibrillation pulse of electrical energy is delivered to the atria between the defibrillation electrode 64 and the implantable housing 36 of the implantable pulse generator 22. Delivering the defibrillation electrical energy pulse at the predetermined coupling interval time after delivering a final atrial pacing pulse and a final ventricular pacing pulse ensures that the defibrillation electrical energy pulse will fall outside the occurrence of a ventricular T-wave of the heart, and will thus reduce the likelihood of inducing a ventricular fibrillation.

The predetermined coupling interval time after delivering the final atrial pacing pulse and the final ventricular pacing pulse is a programmable value of between approximately 20 to 150 milliseconds, where 85 milliseconds is an appropriate value. The predetermined coupling interval time, however, is not limited to the aforementioned range, and values outside of this range exist which do not depart from the scope of the invention.

Figure 4:
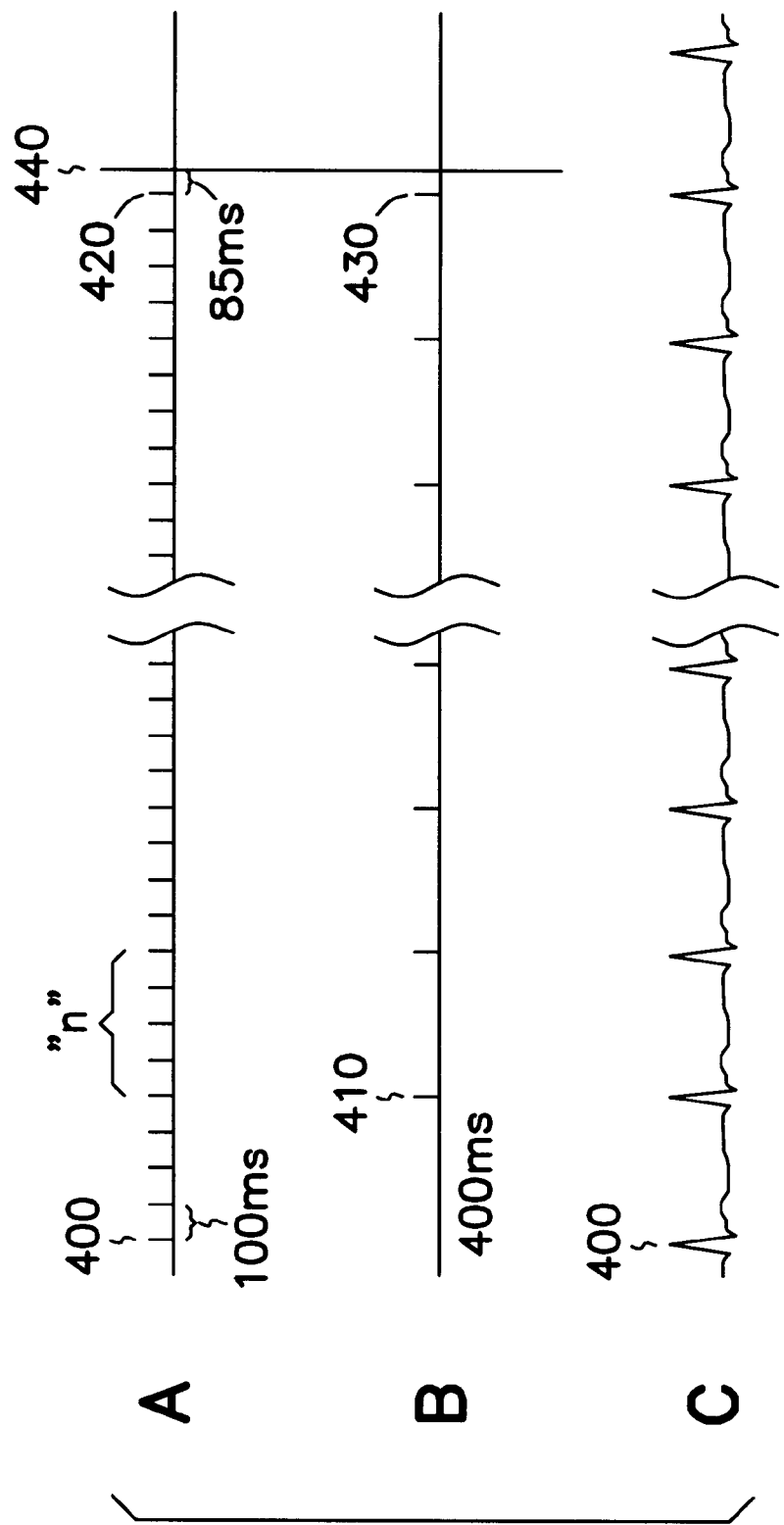
FIG. 4 is a schematic diagram illustrating one embodiment of a timing sequence of pacing and defibrillating pulses according to the present invention.

Referring now to FIG. 4, there is shown a schematic diagram illustrating one embodiment of a timing sequence of pacing and defibrillation electrical energy pulse being delivered to a heart experiencing a supraventricular arrhythmia according to the present invention. The train of atrial pacing pulses is programmed to deliver forty (40) atrial pacing pulses at an interval time between each pacing pulse of 100 ms and is represented by line A of FIG. 4. The programmable pacing scheme duration is programmed to 4 seconds, and the integer value for n is programmed to 4, such that the defibrillation system 20 will deliver the ventricular pacing pulse to the heart with every fourth atrial pacing pulse delivered. Ventricular pacing pulses are shown on line B of FIG. 4. Line C of FIG. 4 is a schematic of an electrocardiogram representing the paced cardiac rhythm of the heart 30.

Upon detecting a supraventricular arrhythmia, the electronic control circuitry of the defibrillation system 20 starts the train of atrial pacing pulses at 400 during a detected R-wave. The atrial pacing pulses shown at line A are delivered at a 100 ms interval and at 410 a first ventricular pacing pulse is delivered to the ventricles about 400 ms after the start of the train of atrial pacing pulses. This pacing scheme reduces the likelihood of the first ventricular pacing pulse from falling on a ventricular T-wave, as the ventricular T-wave typically occurs about 120 milliseconds after the ventricular R-wave. Subsequently, a ventricular pacing pulse is delivered on every fourth atrial pulse of the train which effectively drives the ventricle at a 4:1 rate of the atrial pacing rate.

The defibrillation system 20 proceeds to deliver the synchronized series of atrial and ventricular pacing pulses until a final atrial pacing pulse at 420 and a final ventricular pacing pulse at 430 is delivered on the fortieth atrial pacing pulse and the tenth ventricular pacing pulse. In one embodiment, the final atrial pacing pulses and the final ventricular pacing pulse delivered at 430 are delivered substantially simultaneously to the heart. Then, at a predetermined coupling interval time of 85 milliseconds after delivering a final atrial pacing pulse and a final ventricular pacing pulse, the defibrillation system 20 delivers a defibrillation electrical energy pulse at 440 across the atrial region of the patient's heart 30.

Figure 5:
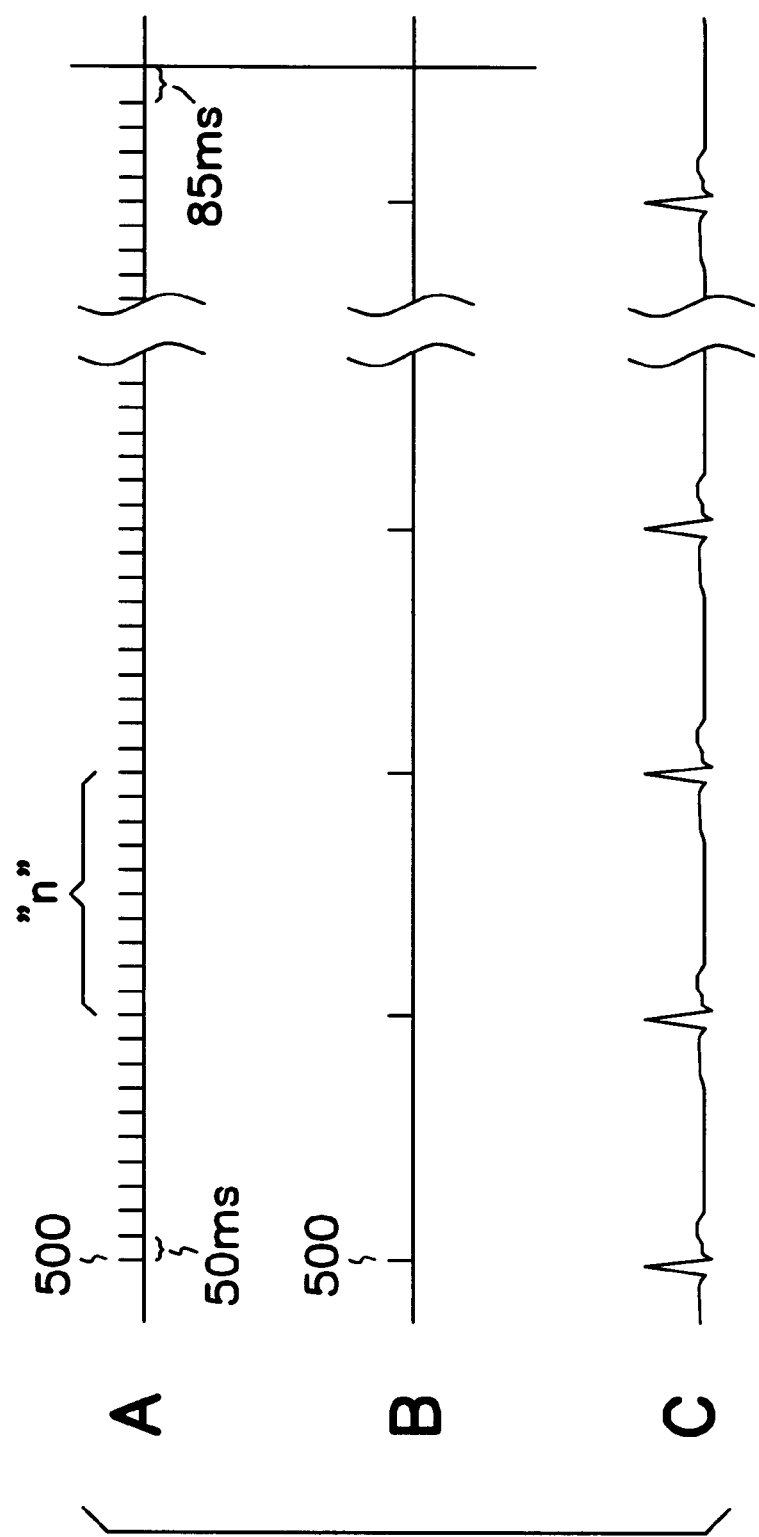
FIG. 5 is a schematic diagram illustrating one embodiment of a timing sequence of pacing and defibrillating pulses according to the present invention.

Referring now to FIG. 5, there is shown a schematic diagram illustrating an additional embodiment of a timing sequence of pacing and defibrillation electrical energy pulse being delivered to a heart experiencing a supraventricular arrhythmia according to the present invention. The train of atrial pacing pulses is programmed to deliver one hundred (100) atrial pacing pulses at an interval time between each pacing pulse of 50 ms and is represented by line A of FIG. 5. The programmable pacing scheme duration is programmed to 5 seconds, and the integer value for n is programmed to 10, such that the defibrillation system 20 will deliver the ventricular pacing pulse to the heart with every tenth atrial pacing pulse delivered. Ventricular pacing pulses are shown on line B of FIG. 5. Line C of FIG. 5 is a schematic of an electrocardiogram representing the paced cardiac rhythm of the heart 30.

Upon detecting a supraventricular arrhythmia, the electronic control circuitry of the defibrillation system 20 starts the synchronized atrial and ventricular pacing pulses by delivering an initial concurrent atrial and ventricular pacing pulses at 500. The atrial pacing pulses shown on line A are delivered at a 50 milliseconds and ventricular pacing pulses are subsequently delivered on every tenth atrial pulse of the train which effectively drives the ventricle at a 10:1 rate of the atrial pacing rate.

The defibrillation system 20 proceeds to deliver the synchronized series of atrial and ventricular pacing pulses until a final atrial pacing pulse at 520 and a final ventricular pacing pulse at 530 is delivered on the one hundred atrial pacing pulse and the eleventh ventricular pacing pulse. In one embodiment, the final atrial pacing pulses and the final ventricular pacing pulse delivered at 530 are delivered substantially simultaneously to the heart. Then, at a predetermined coupling interval time of 85 milliseconds after delivering a final atrial pacing pulse and a final ventricular pacing pulse, the defibrillation system 20 delivers a defibrillation electrical energy pulse at 540 across the atrial region of the patient's heart 30.

We claim:

1. A method of treating a heart, comprising the steps of:
upon detecting a supraventricular arrhythmia, delivering a train of atrial pacing pulses to an atrial region of the heart and a series of ventricular pacing pulses to a ventricular region of the heart, where the series of ventricular pacing pulses is synchronized with the train of atrial pacing pulses; and
delivering a defibrillation electrical energy pulse across the atrial region at a predetermined coupling interval time after delivering a final atrial pacing pulse and a final ventricular pacing pulse.

2. The method according to claim 1, including synchronizing each ventricular pacing pulse of the series of ventricular pacing pulses with every nth pacing pulse of the train of atrial pacing pulses, where n is a programmable integer value greater than or equal to 3 and less than or equal to 50.

3. The method according to claim 1, where the step of delivering a train of atrial pacing pulses further includes the step of delivering a first atrial pacing pulse to the atrial region of the heart during a detected ventricular R-wave.

4. The method according to claim 1, where the step of delivering a train of atrial pacing pulses and a series of ventricular pacing pulses further includes the step of delivering an initial concurrent atrial and ventricular pacing pulse.

5. The method according to claim 1, where delivering the train of atrial pacing pulses and the series of ventricular pacing pulses occurs over a programmable pacing scheme duration.

6. The method according to claim 5, where the step of delivering the train of atrial pacing pulses and the series of ventricular pacing pulses further includes the step of charging a defibrillator capacitor during the programmable pacing scheme duration.

7. The method according to claim 5, including programming a value in the range between 2 to 30 seconds for the programmable pacing scheme duration.

8. The method according to claim 1, including programming a pacing rate that is at least 10 beats per minute above a patient's intrinsic ventricular rate for the series of ventricular pacing pulses.

9. The method according to claim 1, including programming the train of atrial pacing pulses having a set number of atrial pacing pulses programmed in the range of between approximately 10 to 1000 pacing pulses.

10. The method according to claim 1, including delivering atrial pacing pulses of the train of atrial pacing pulses at a programmable atrial pacing interval, where the programmable atrial pacing interval is set to a value between 20 to 50 milliseconds.

11. The method according to claim 1, where the pacing pulses of the train of atrial pacing pulses are delivered at a programmed energy level value set between 0.01 to 1 Joules.

12. The method according to claim 1, where the step of delivering a defibrillation electrical energy pulse further includes the step of monitoring the ventricular region of the heart prior to delivering the final atrial pacing pulse and the final ventricular pacing pulse to determine if a premature ventricular contraction has occurred.

13. The method according to claim 12, further including the step of repeating delivering the train of atrial pacing pulses and the series of ventricular pacing pulses upon monitoring a premature ventricular contraction prior to delivering the final atrial pacing pulse and the final ventricular pacing pulse.

14. The method according to claim 12, further including the step of delivering a predetermined number of additional atrial pacing pulses and ventricular pacing pulses to the heart upon detecting a premature ventricular contraction.

15. The method according to claim 14, including programming a number of pacing pulses in the range between 10 to 1000 pacing pulses for the predetermined number of additional atrial pacing pulses, and synchronizing the additional ventricular pacing pulses to occur with every nth pacing pulse of the additional atrial pacing pulses, where n is a programmable integer value greater than or equal to 3 and less than or equal to 50.

16. The method according to claim 1, including delivering the defibrillation electrical energy pulse at the predetermined coupling interval time after the final atrial pacing pulse and the final ventricular pacing pulse so that the defibrillation electrical energy pulse will fall outside the occurrence of a T-wave of the heart.

17. The method according to claim 1, where the final atrial pacing pulses and the final ventricular pacing pulse are delivered substantially simultaneously.

18. The method according to claim 1, including programming the predetermined coupling interval time to a programmable value of between 20 to 150 milliseconds.

19. The method according to claim 1, including programming the defibrillation electrical energy pulse to a programmable value set between 1 to 10 Joules.

20. A method of treating a heart, comprising the steps of:
upon detecting an occurrence of a supraventricular arrhythmia, delivering a train of atrial pacing pulses to an atrial region of the heart and a series of ventricular pacing pulses to a ventricular region of the heart, where a first atrial pacing pulse is delivered to the atrial region of the heart during a detected ventricular R-wave, the train of atrial pacing pulses has a set number of atrial pacing pulses programmed in the range of between approximately 10 to 1000 pacing pulses, the atrial pacing pulses are delivered at a programmable atrial pacing interval set to a value between approximately 20 to 50 milliseconds and a programmed energy level value set between 0.01 to 1 Joules, and where each ventricular pacing pulse of the series of ventricular pacing pulses is synchronized to occur with every nth pacing pulse of the train of atrial pacing pulses, where n is a programmable integer value greater than or equal to 3 and less than or equal to 50; and
delivering a defibrillation electrical energy pulse across the atria region at a predetermined coupling interval time after delivering a final atrial pacing pulse and a final ventricular pacing pulse so that the defibrillation electrical energy pulse will fall outside the occurrence of a T-wave of the heart, where the defibrillation electrical energy pulse is a programmable value set between 1 to 10 Joules and the predetermined coupling interval time is a programmable value of between approximately 20 to 150 milliseconds.

21. The method according to claim 20, where the step of delivering a train of atrial pacing pulses further includes the step of delivering a first atrial pacing pulse to the atrial region of the heart during a detected ventricular R-wave.

22. The method according to claim 20, where the step of delivering a train of atrial pacing pulses and a series of ventricular pacing pulses further includes the step of delivering an initial concurrent atrial and ventricular pacing pulse.

23. The method according to claim 20, where the final atrial pacing pulses and the final ventricular pacing pulse are delivered substantially simultaneously.

24. A defibrillation system, comprising:
an implantable housing;
electronic control circuitry within the implantable housing;
a ventricular catheter attached to the implantable housing of the defibrillation system, where the ventricular catheter has at least one ventricular pacing electrode connected to the electronic control circuitry and is positioned within the heart with the at least one ventricle pacing electrode in a right ventricle chamber of the heart;
an atrial catheter attached to the implantable housing of the defibrillation system, where the atrial catheter has at least one atrial pacing electrode and at least one defibrillation electrode connected to the electronic control circuitry and is positioned within the heart with the at least one atrial pacing electrode and the at least one defibrillation electrode in the supraventricular region of the heart; and
where the electronic control circuitry receives cardiac signals through both the at least one ventricular pacing electrode and the at least one atrial pacing electrode, and the electronic control circuitry, upon detecting a supraventricular arrhythmia, delivers a train of atrial pacing pulses across the at least one atrial pacing electrode, and a series of ventricular pacing pulses across the at least one ventricular pacing electrode, where the series of ventricular pacing pulses is synchronized with the train of atrial pacing pulses, and delivers a defibrillation electrical energy pulse across the atrial region at a predetermined coupling interval time after delivering a final atrial pacing pulse and a final ventricular pacing pulse.

25. The defibrillation system according to claim 24, where each ventricular pacing pulse of the series of ventricular pacing pulses is synchronized to occur with every nth pacing pulse of the train of atrial pacing pulses, where n is a programmable integer value greater than or equal to 3 and less than or equal to 50.

26. The defibrillation system according to claim 24, where the train of atrial pacing pulses has a first pacing pulse that is delivered during a detected ventricular R-wave.

27. The defibrillation system according to claim 24, where the defibrillation system delivers an initial concurrent atrial and ventricular pacing pulse of the train of atrial pacing pulses and the series of ventricular pacing pulses upon detecting a supraventricular arrhythmia.

28. The defibrillation system according to claim 24, where the implantable housing has an exposed electrically conductive surface and the defibrillation electrical energy pulse is delivered between the exposed electrically conductive surface of the implantable housing and the at least one defibrillation electrode.

29. The defibrillation system according to claim 24, where the atrial catheter includes two defibrillation electrodes, and the atrial catheter is positioned within the heart with the atrial pacing electrode, the two defibrillation electrodes in the supraventricular region of the heart; and where defibrillation electrical energy is delivered between the two defibrillation electrodes.

30. The defibrillation system according to claim 29, where the defibrillating electrical energy provided to the patient's heart are biphasic pulses delivered between the two defibrillation electrodes.

31. The defibrillation system according to claim 29, where the implantable housing has an exposed electrically conductive surface and the two defibrillation electrodes are electrically connected such that the defibrillating electrical energy provided to the heart are biphasic pulses delivered between the electrically connected defibrillation electrodes and the exposed electrically conductive surface of the implantable housing.

* * * * *